United States Patent [19]
Miyata et al.

[11] Patent Number: 5,695,467
[45] Date of Patent: Dec. 9, 1997

[54] INTRA AORTIC BALLOON PUMPING CATHETER

[75] Inventors: Shinichi Miyata; Tetsuo Toyokawa; Kouichi Sakai; Satoshi Morikawa, all of Yokohama, Japan

[73] Assignee: Nippon Zeon Co., Ltd., Tokyo, Japan

[21] Appl. No.: 472,774

[22] Filed: Jun. 7, 1995

Related U.S. Application Data

[63] Continuation of Ser. No. 187,728, Jan. 28, 1994, abandoned.

[30] Foreign Application Priority Data

Feb. 8, 1993 [JP] Japan ............................ 5-020084
Aug. 13, 1993 [JP] Japan ............................ 5-201404

[51] Int. Cl.⁶ ............................................ A61M 29/00
[52] U.S. Cl. ................................ 604/96; 604/280
[58] Field of Search ................ 604/96–103, 280, 604/282; 606/192, 194

[56] References Cited

U.S. PATENT DOCUMENTS

5,433,713  7/1995  Trotta ........................... 604/264

Primary Examiner—Corrine M. McDermott
Attorney, Agent, or Firm—Nikaido, Marmelstein, Murray & Oram LLP

[57] ABSTRACT

A catheter having a catheter tube. The catheter tube is comprised of a base tube comprised of a hard plastic with a linear elastic modulus of at least 100 kg/mm² and a surface tube of an anti-thrombogenic material covering the outer circumference of the base tube. Further, The present invention provides a catheter set which is used when inserting the catheter and the like into the blood vessel of a patient. The catheter set comprises a retaining sheath whose distal end is inserted into a blood vessel and which has a hemostatic valve at its proximal end, a catheter having a catheter tube, which is inserted from the proximal end of the retaining sheath and thereby inserted into the blood vessel, and a holding ring for affixing said retaining sheath to the outer circumference of said catheter tube at any position in the axial direction.

4 Claims, 12 Drawing Sheets

INTRA AORTIC BALLOON PUMPING CATHETER

This application is a continuation of application Ser. No. 08/187,728, filed on Jan. 28, 1994 now abandoned.

BACKGROUND OF THE INVENTION

1. Field of the Invention

The present invention relates to a catheter set, a catheter and a method for production thereof. The catheter set is used when inserting the catheter and the like into the blood vessel of a patient.

2. Description of the Related Art

In the intra-aortic balloon pumping (IABP) method used for treatment of cardiac insufficiency and other kinds of deterioration of cardiac functions, such as the percutaneous coronary angioplasty (PTCA) method used for treatment such as expanding the blood vessels around the heart, the thermal dilution catheter (TDC) method used for measuring the amount of blood flow of the heart, and the aorta bypass catheter method using a catheter for assistant circulation and other treatment methods, a catheter is inserted into the arterial blood vessel of the patient. To insert the catheter into the blood vessel of the patient, a catheter set including a needle, sheath, positioning plug, etc. in addition to the catheter is required. For example, first the needle and sheath are used to form an incision in the blood vessel of the patient, the needle is withdrawn, and the catheter is passed inside the sheath, thereby inserting the catheter into the blood vessel.

There are a splitable sheath of the type where the sheath is divided in the axial direction after insertion of the catheter into the patient's blood vessel (for example, see Japanese Unexamined Patent Publication (Kokai) No. 63-252168) and the retaining sheath of the type where the sheath is not removed even after insertion of the catheter.

These two types of sheaths each have their advantages and disadvantages. For example, the former splitable sheath had the problem of bleeding when dividing the sheath and the problem of work efficiency. The retaining sheath has a hemostatic valve comprised of a rubber film etc. at the proximal end, so does not have the problem of the splitable sheath, but has the problem mentioned below.

Bleeding results if the retaining sheath is pulled out from the blood vessel of the patient, so it is necessary to affix the proximal end of the retaining sheath to the skin of the patient by suturing or other means. Further, the distal end of the catheter has to be retained at a predetermined position in the blood vessel, so after inserting the catheter into the blood vessel, it was necessary to affix the outside end of the catheter to the patient. Accordingly, in the prior art, a positioning plug had to be attached to the outside end of the catheter so as to be movable in the axial direction of the catheter, the positioning plug had to be affixed to the catheter at a predetermined position in the axial direction of the catheter projecting out from the retaining sheath to the outside of the body, and the positioning plug had to be affixed to the skin of the patient by suturing or other means. Further, the connector attached to the outside proximal end of the catheter had to be affixed to the skin of the patient by suturing or other means.

That is, in the prior art it was necessary to affix the retaining sheath and the positioning plug separately to the skin of the patient. The work for affixing these was complicated and the portion to be disinfected was large, so a more preferable means has been required.

Further, the catheter preferably has a certain degree of rigidity since it is inserted along the arterial blood vessel. The catheter preferably has a certain degree of flexibility since the catheter, further, is inserted inside the winding blood vessel of a patient. Also the catheter preferably is comprised of an anti-thrombogenic material since it is inserted into the arterial blood vessel.

If the rigidity of the catheter is too stiff, there is a danger of damaging the blood vessel of the patient while inserting the catheter inside the patient's blood vessel, so this is not preferable. Conversely, if the flexibility of the balloon catheter is too soft, the catheter is pushed back by the flow of blood after being in the predetermined position of the artery. The catheter has to be in the predetermined position of the artery in order to obtain a certain effect of the catheter, so the high flexibility of the balloon catheter is not preferable either. If the catheter is a balloon catheter for IABP, it is important that a balloon portion is positioned in the arterial blood vessel as close to the heart as possible for the pumping action. Further, if the balloon portion is pushed back, there is a danger of blocking the renal artery, which branches from the abdominal aorta, so this is not preferred either. In addition, if the catheter is comprised of a material with inferior anti-thrombogenic property, thrombus will accumulate on the catheter and there would be the danger of obstructing the peripheral blood flow, which is also not preferable.

In the prior art, however, it was difficult to produce a catheter which satisfied all these demands. Catheters had to be made sacrificing one of these demands. For example, when giving priority to anti-thrombogenic property and making the catheter from a polyurethane resin, there was the danger of the catheter being pushed back by the flow of blood since the elasticity of polyurethane resin tends to fall remarkably due to the body temperature.

SUMMARY OF THE INVENTION

The present invention has been made in consideration of this situation and has as its first object the provision of a novel catheter set which prevents to a great extent the bleeding from the insertion into the blood vessel, lightens the discomfort on the patient, and is superior in work efficiency.

The present invention has as its second object the provision of a catheter which can be easily inserted into the blood vessel of a patient, which enables the catheter to be inserted to the prescribed position in the blood vessel, which will not be pushed back by the flow of blood, and further which is superior in anti-thrombogenic property, and to a method for production of the same.

To achieve the above first object, the catheter set according to one aspect of the present invention is a catheter set comprising a retaining sheath whose distal end is inserted into a blood vessel and which has a hemostatic valve at its proximal end, a catheter having a catheter tube, which is inserted from the proximal end of said retaining sheath and thereby inserted into the blood vessel, and a holding means for affixing said retaining sheath to the outer circumference of said catheter tube at any position in the axial direction.

Said holding means preferably comprises a positioning plug which is attached slidingly in the axial direction to the outer circumference of the proximal end of said catheter tube and is able to affix to the outer circumference of said catheter tube at any position in the axial direction, mutually detachable or connectable connection portion being formed at least at one of said retaining sheath and positioning plug.

Said positioning plug preferably has a holding ring which can press against the outer circumference of the catheter tube by being compressed in the axial direction so as to be affixed to the outer circumference of said catheter tube at any position in the axial direction.

Said positioning plug preferably comprises a plug body which is able to be connected detachably to said retaining sheath and a cap which is connected to said plug body by screwing, and said holding ring is attached between said plug body and said catheter tube so as to be compressed in the axial direction by screwing said cap on said plug body.

Said plug body preferably has a threaded projection which is able to detachably engage with a flange portion of said retaining sheath.

One of said retaining sheath and said positioning plug preferably has a handle for affixing to a body surface of a patient by fixing means.

In the catheter set according to the first aspect of the present invention, first the retaining sheath is inserted into the blood vessel and then the catheter tube is inserted through the retaining sheath to the prescribed position in the blood vessel. At this time, since the hemostatic valve is attached to the proximal end of the retaining sheath, it is possible to prevent to a great extent bleeding of the patient.

After this, the positioning plug attached to the outer circumference of the outside end of the Catheter tube so as to be movable in the axial direction is moved along the axial direction of the catheter tube in the direction of the insertion of the blood vessel, that is, in the direction of the retaining sheath. Then, the retaining sheath and the positioning plug are mutually connected. At this point of time, the outer circumference of the catheter tube is affixed to the positioning plug. Then, by affixing to the skin of the patient one of the retaining sheath or positioning plug, it is possible to simultaneously affix the retaining sheath to the patient and position the catheter tube. Accordingly, in the present invention, the portion affixed to the skin of the patient becomes smaller, the on the patient can be lightened, and further the portion to be disinfected becomes small and the work efficiency is improved.

A catheter set according to another aspect of the present invention comprises a retaining sheath whose distal end is inserted into a blood vessel and which has a hemostatic valve at its proximal end and a catheter having a catheter tube, which is inserted from the proximal end of the retaining sheath and thereby inserted into the blood vessel, said retaining sheath having attached to it a holding ring which can press against the outer circumference of said catheter tube by being compressed in the axial direction so as to be affixed to the outer circumference of said catheter tube at any position in the axial direction.

Said retaining sheath preferably comprises a sheath base having a sheath body whose distal end is inserted to the blood vessel and a cap which is connected to said sheath body by screwing, and said holding ring is attached between said sheath body and said catheter tube so as to be compressed in the axial direction by screwing said cap on said sheath base.

Said cap preferably has said hemostatic valve at the proximal end thereof. Said retaining sheath preferably has a handle for affixing to a body surface of a patient by fixing means.

Said catheter preferably has a balloon portion connected to a distal end of said catheter tube so that said balloon portion expands and contracts in timing with a heart beating and said balloon catheter set is used for intra-aortic balloon pumping.

In the catheter set according to the second aspect of the present invention, first the retaining sheath is inserted into the blood vessel and then the catheter tube is inserted through the retaining sheath to the prescribed position in the blood vessel. At this time, since the hemostatic valve is attached to the proximal end of the retaining sheath, it is possible to prevent to a great extent bleeding of the patient.

After this, the retaining sheath is operated and the holding ring is made to compress in the axial direction. As a result, the outer circumference of the catheter tube is affixed to the sheath and the catheter tube is positioned with respect to the retaining sheath. Next, by affixing the retaining sheath to the skin of the patient, the retaining sheath can be affixed to the patient and the catheter tube positioned simultaneously. Accordingly, in the present invention, the portion affixed to the skin of the patient becomes smaller, the discomfort on the patient can be lightened, and further the portion to be disinfected becomes smaller and the efficiency is improved.

To achieve the above second object, the catheter according to the present invention is a catheter comprising a catheter tube, said catheter tube being comprised of a base tube comprised of a hard plastic with a linear elastic modulus of at least 100 kg/mm$^2$ and a surface tube of an anti-thrombogenic material covering the outer circumference of the base tube.

Said base tube is preferably comprised of one of the group of a polyamide resin, polyimide resein, a fluorocarbon resin, and a polyvinyl difluoride resin and said surface tube is comprised of a polyurethane resin.

Said surface tube may be formed integrally with a balloon film constituting a balloon portion which is connected to a distal end of said catheter tube.

Said catheter preferably has a balloon portion connected to a distal end of said catheter tube so that a shuttle gas is introduced and released into and from said balloon portion and said balloon portion expands and contracts in timing with a heart beating.

To achieve the above second object, the method for production of a catheter according to the present invention is a method for production of a catheter having a catheter tube comprising a step of forming a base tube comprised of a hard plastic with a linear elastic modulus of at least 100 kg/mm$^2$, a step of forming a surface tube of an anti-thrombogenic material, and a step of covering the outer circumference of said base tube with said surface tube so as to make said catheter tube.

Said catheter tube comprised of said base tube and surface tube may be formed by two-layer extrusion.

Said surface tube may also be made by forming and drying a solution layer at the outer circumference of said base tube.

A polyisocyanate type adhesive is preferably provided between said base tube and surface tube.

A balloon film is preferably formed integrally with said surface tube at the same time as when said surface tube is made by forming and drying said solution layer at the outer circumference of said base tube.

In the catheter of the present invention, the catheter tube has a double-tube construction, with the inside base tube comprised of a hard plastic with a linear elastic modulus of at least 100 kg/mm$^2$ and with the outside surface tube comprised of an anti-thrombogenic material. Therefore, the catheter tube has a suitable rigidity and can be easily inserted into the patient's blood vessel and, also, the balloon portion connected to the distal end of the catheter tube will not be pushed back by the blood flow etc. after being set at the prescribed position in the patient's blood vessel.

Further, the outside surface tube is comprised of a material superior in anti-thrombogenic action, so there is little danger of adhesion of thrombus.

Still further, according to the method for production of a catheter according to the present invention, it is possible to produce a catheter with such superior characteristics extremely easily and at a low cost.

DESCRIPTION OF THE PREFERRED EMBODIMENTS

Below, catheters according to preferred embodiments of the present invention will be explained in more detail referring to the drawings.

First Embodiment

The applications of a catheter set according to the present invention are not particularly limited, but the set may be used for example for the IABP method, PTCA method, TDC method, aorta bypass catheter method and other forms of treatment. In the following explanation, reference is made to an embodiment of use of the catheter set for the IABP method.

Figure 1:
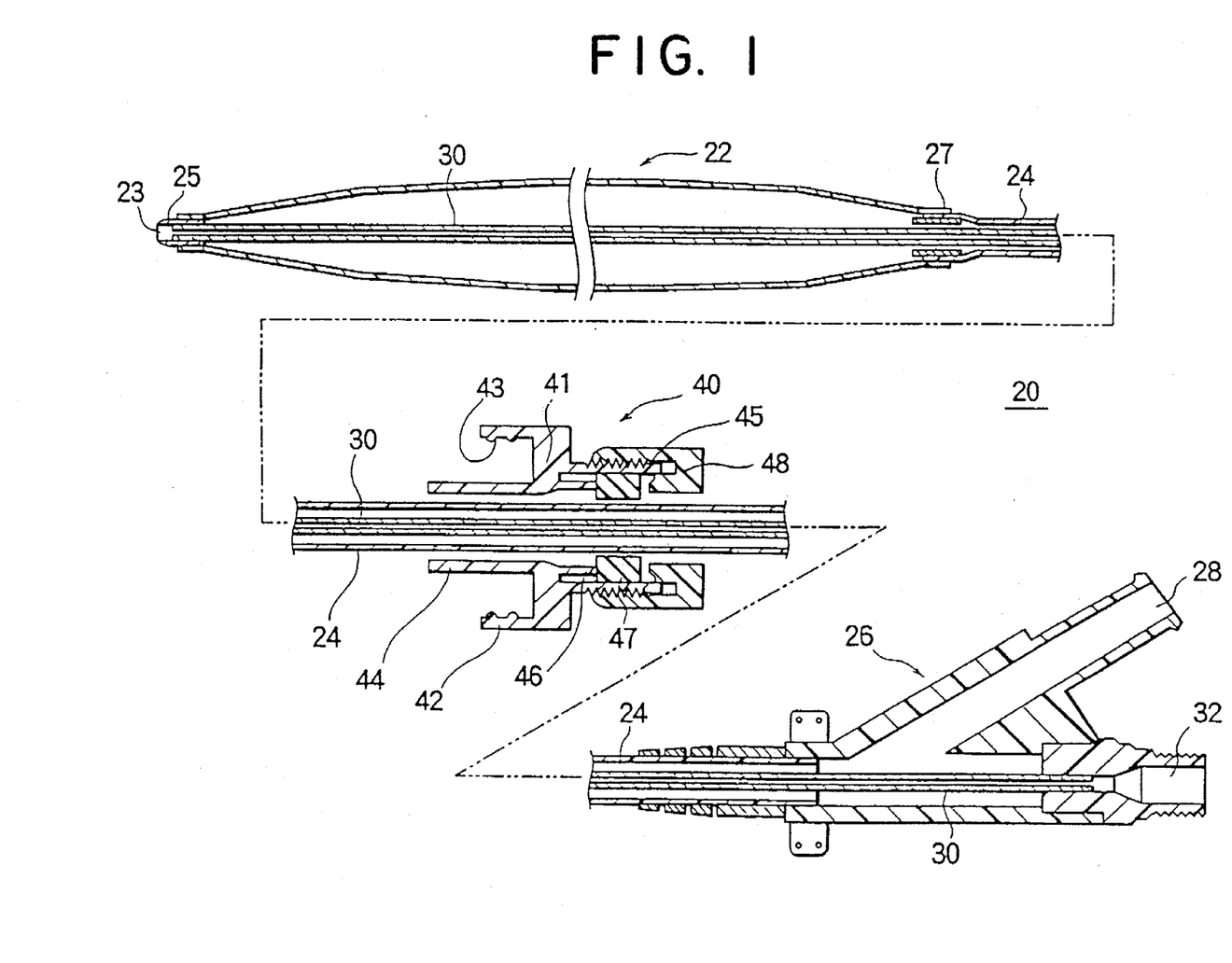
FIG. 1 is a schematic cross-sectional view of a balloon catheter according to a first embodiment of the present invention.
Figure 2:
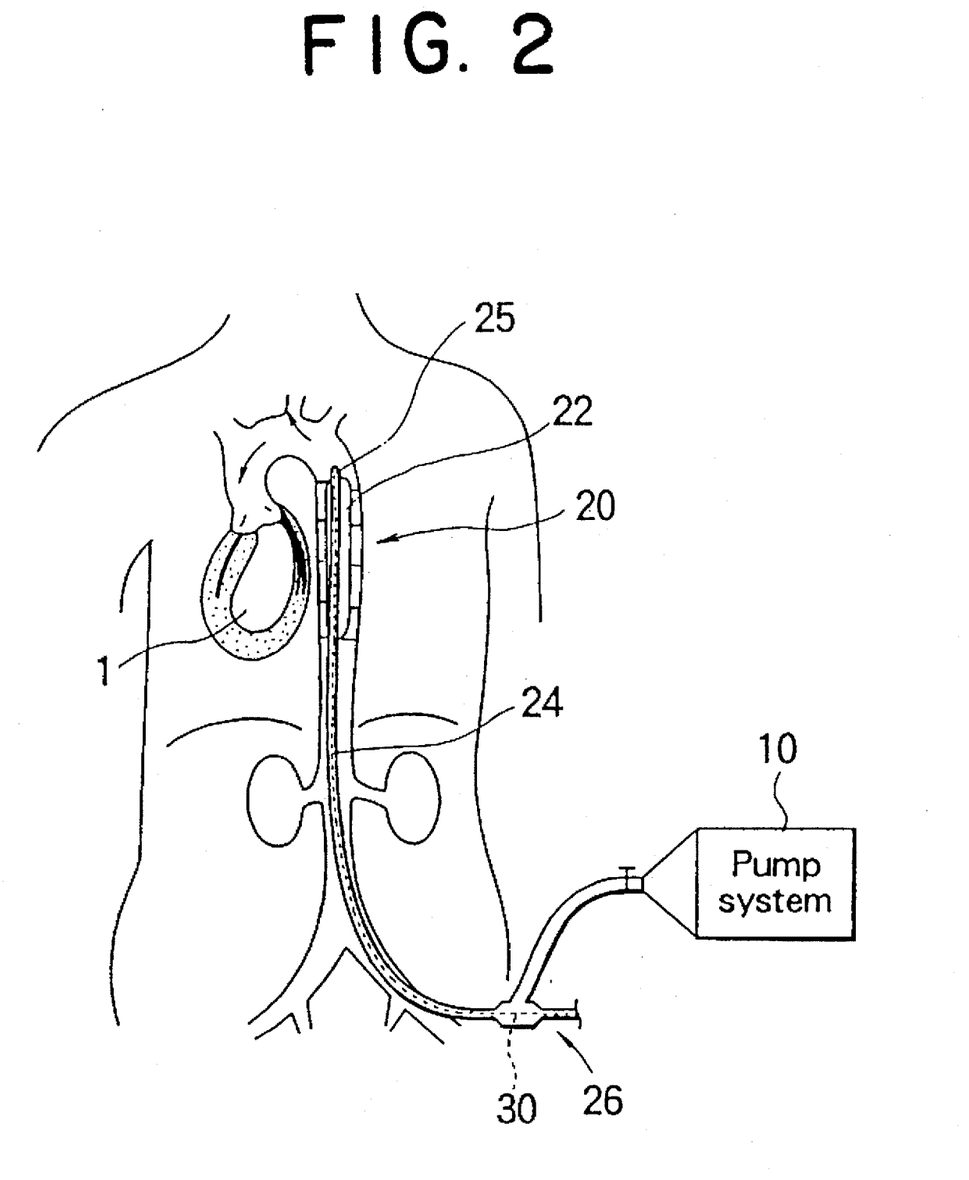
FIG. 2 is a schematic view showing an example of use of the balloon catheter.

In the IABP method, use is made of a balloon catheter 20 shown in FIGS. 1 and 2. The balloon catheter 20 has a balloon portion 22 which expands and contracts in timing with the heart beating. The balloon portion 22 is comprised of a thin film of a thickness of about 100 to 150 μm. The material of the thin film is not particularly limited, but preferably is a material superior in resistance to flexural fatigue, for example, is made of polyurethane. The outer diameter and length of the balloon portion 22 are determined in accordance with the inner volume of the balloon portion 22, which has a great effect on the effect of assisting the heart beat, the inner diameter of the arterial blood vessel, and the like. The inner volume of the balloon portion 22 is not particularly limited, but may be 30 to 50 cc. The outer diameter of the balloon portion 22 is preferably 14 to 16 mm, and the length is preferably 210 to 270 mm.

At the distal end of the balloon portion 22 there is attached by a means such as heat bonding or adhesion a front tip portion 25 with a blood port 23 formed in it.

At the inner circumference of the front tip portion 25 is attached the distal end of the inner tube 30 by heat bonding or adhesion.

The inner tube 30 is comprised for example of a stainless steel tube, a spring reinforced plastic tube or a resin tube etc. and extends substantially concentrically in the axial direction inside the balloon portion 22 and the catheter tube 24 and is communicated with the later mentioned blood pressure measurement port 32 of the bifurcation 26. The inside of the inner tube 30 is not communicated with the inside of the balloon portion 22. The inner tube 30 positioned in the balloon portion 22 is also used as the guide rod at the time of inserting the balloon catheter 20 in the artery. The contracted balloon portion 22 is wound on it for easy insertion of the balloon portion 22 in the artery.

The inner tube 30 may be preferably positioned substantially in a concentric manner with the balloon portion 22 and be preferably continuously affixed to the inside wall of the catheter tube 24 from the proximal end of the balloon portion 22 to the bifurcation 26 which is detailed later. In this embodiment, the response characteristic of inflation and deflation of the balloon portion 22 is remarkably improved as shown in U.S. patent application Ser. No. 903,770.

At the proximal end of the balloon portion 22 at the outer circumference of a metal connecting tube 27 is connected the distal end of the catheter tube 24. The shuttle gas is introduced to or released from the inside of the balloon portion 22 through the catheter tube 24 so as to make the balloon portion 22 expand or contract. The balloon portion 22 and the catheter tube 24 are connected by heat bonding or adhesion by an adhesive such as an ultraviolet ray curable resin.

The material of the catheter tube 24 is not particularly limited, but use may be made of polyurethane, polyvinyl chloride, polyethylene, polyamide, etc. The inside diameter of the catheter tube 24 is preferably 1.5 to 4.0 mm. The thickness of the catheter tube 24 is preferably 0.05 to 0.4 mm.

At the proximal end of the catheter tube 24 is connected the bifurcation 26 positioned outside the patient's body. The bifurcation 26 is formed separate from the catheter tube 24 and is affixed by a means such as heat bonding or adhesion, but it may also be formed integrally with the catheter tube 24. At the bifurcation 26 are formed a shuttle gas port 28 for introducing or releasing shuttle gas into or from the inside of the catheter tube 24 and the balloon portion 22 and a blood pressure measurement port 32 communicated with the inside of the inner tube 30.

The shuttle gas port 28 is connected to a driving console 10, for example, as shown in FIG. 2. This driving console 10 is used to introduce or release the shuttle gas in or from the balloon portion 22. The gas which is introduced is not particularly limited, but use may be made of helium gas etc., having a small viscosity, so that the balloon portion can expand or contract quickly in accordance with the operation of the driving console 10. The driving console 10 is not particularly limited, but use may be made for example of the one disclosed in Japanese Examined Patent Publication No. 2-39265.

The blood pressure measurement port 32 is connected for example to a blood pressure measurement apparatus, which can measure the fluctuations in the pressure of the arterial blood near the blood port 23. The heart beating is detected based on the fluctuations in the blood pressure measured by the blood pressure measurement apparatus, and the driving console 10 shown in FIG. 2 is controlled in accordance with the heart beating to make the balloon portion 22 expand or contract.

In this embodiment, a positioning plug 40 is attached to the outer circumference of the catheter tube 24 positioned between the bifurcation 26 and balloon portion 22 so as to be movable along the axial direction of the catheter tube 24. The positioning plug 40 has a plug body 41. The plug body 41 has a first outer tube 42 which is able to be connected detachably to the flange portion 51 of the retaining sheath 50 shown in FIG. 3. At the inner circumference side of the first outer tube 42 is formed a threaded projection 43, which engages with the flange portion 51 of the retaining sheath 50 shown in FIG. 3.

Figure 7:
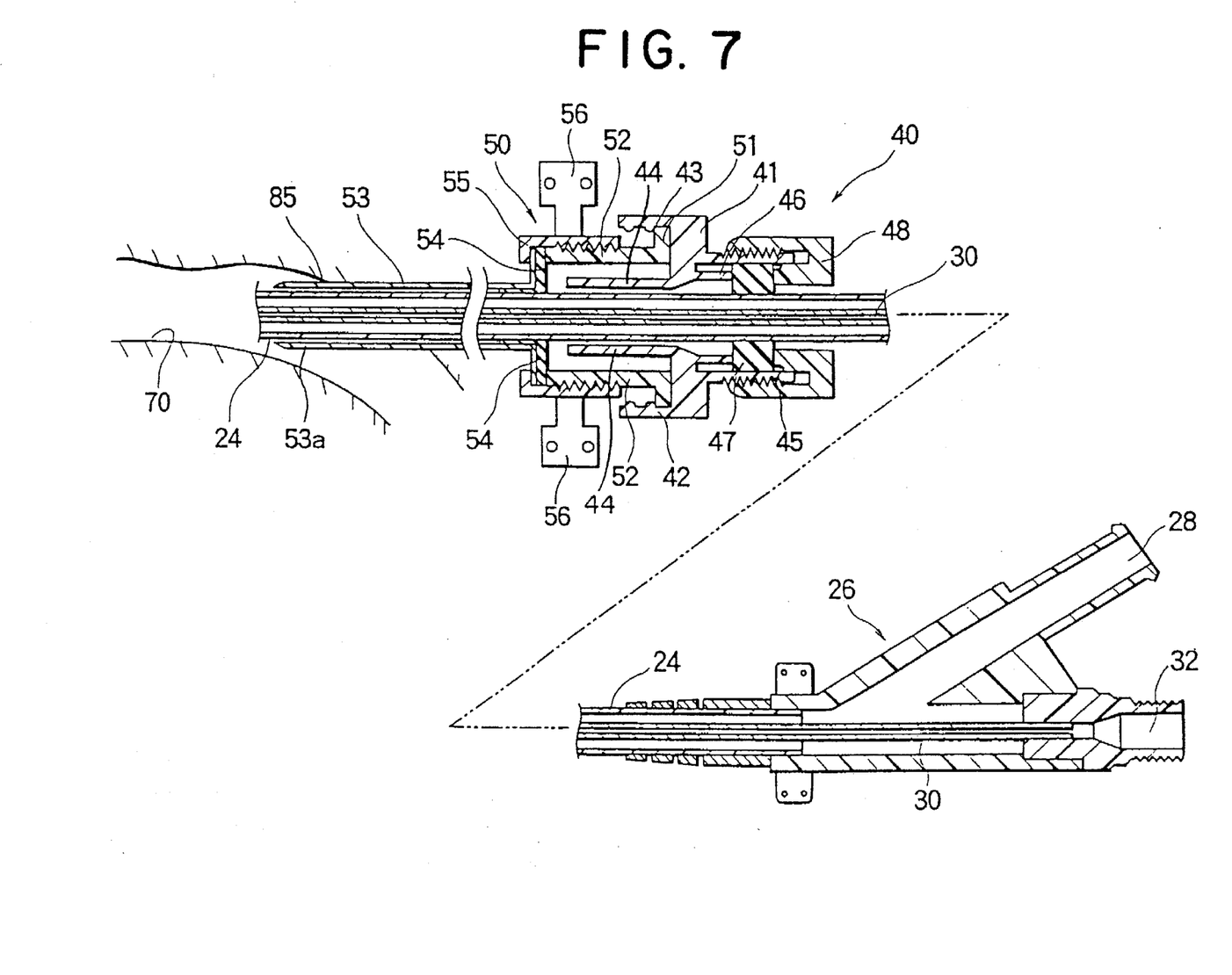
FIG. 7 is a cross-sectional view showing the method of use of the balloon catheter set.

At the plug body 41 on the inner circumference side of the first outer tube 42 is formed the first inner tube 44. The first inner tube 44, as shown in the later FIG. 7, is allowed to be inserted into the sheath base portion 52 of the retaining sheath 50. Further, as shown in FIG. 1, the plug body 41 has formed substantially concentrically a second outer tube 45 and second inner tube 46 at the side opposite to the first outer tube 42 and the first inner tube 44. At the outer circumference of the second outer tube 45 is screwed the cap 48. At the inner circumference side of the second outer tube 45 is attached an elastic holding ring 47. By screwing the cap 48 on the second outer tube 45, the holding ring 47 is compressed and elastically deforms in the axial direction, becomes smaller in inside diameter, and presses against the outer circumference of the catheter tube 24. That is, by screwing the cap 48 on the plug body 41, the holding ring 47 deforms and presses against the outer circumference of the catheter tube 24 so that the positioning plug 40 can be affixed at any position of the catheter tube 24.

The holding ring 47 is made of an elastic material, for example, is made of silicone rubber, fluororubber, natural rubber, polyurethane, etc. In this embodiment, the JIS hardness of the holding ring 47 is at least 52, preferably from 55 to 70. The inner diameter of the holding ring 47 is not particularly limited, but is preferably the same diameter or 50 to 300 µm larger than the outer diameter of the catheter tube 24. Further, the outer diameter of the holding ring 47 is preferably about 50 to 300 µm smaller than the inner diameter of the second outer tube 45 positioned at the outer circumference of the holding ring 47. Also, the thickness of the holding ring 47 in the radial direction is preferably 0.25 to 1.5 times the outer diameter of the catheter tube 24.

In this embodiment, use is made of the catheter set described in detail below for inserting the balloon portion 22 and catheter tube 24 of the balloon catheter of this construction into the blood vessel of a patient.

Figure 3:
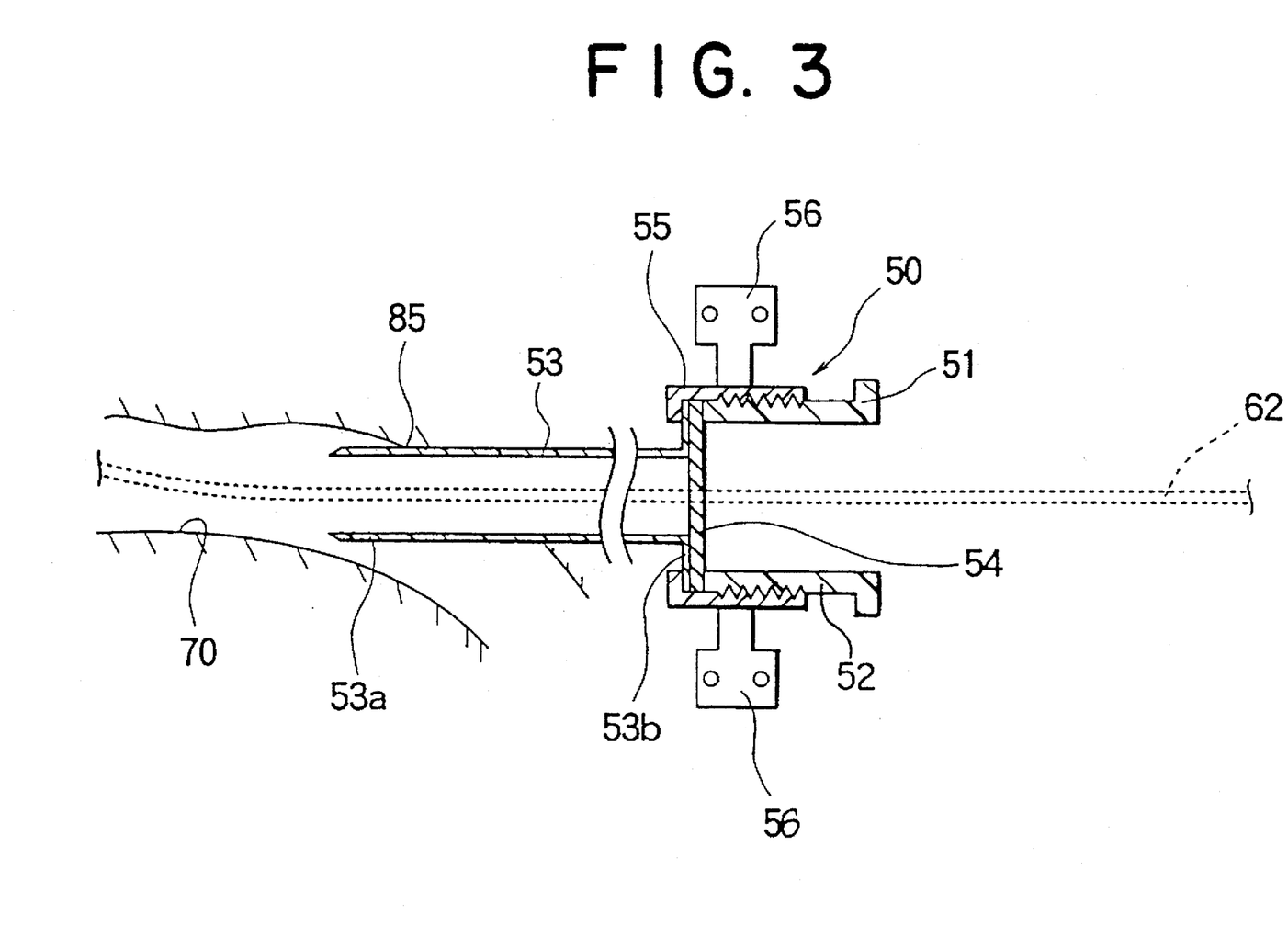
FIG. 3 is a cross-sectional view of key portions showing the state of use of the retaining sheath used in the balloon catheter set according to the embodiment.
Figure 5:
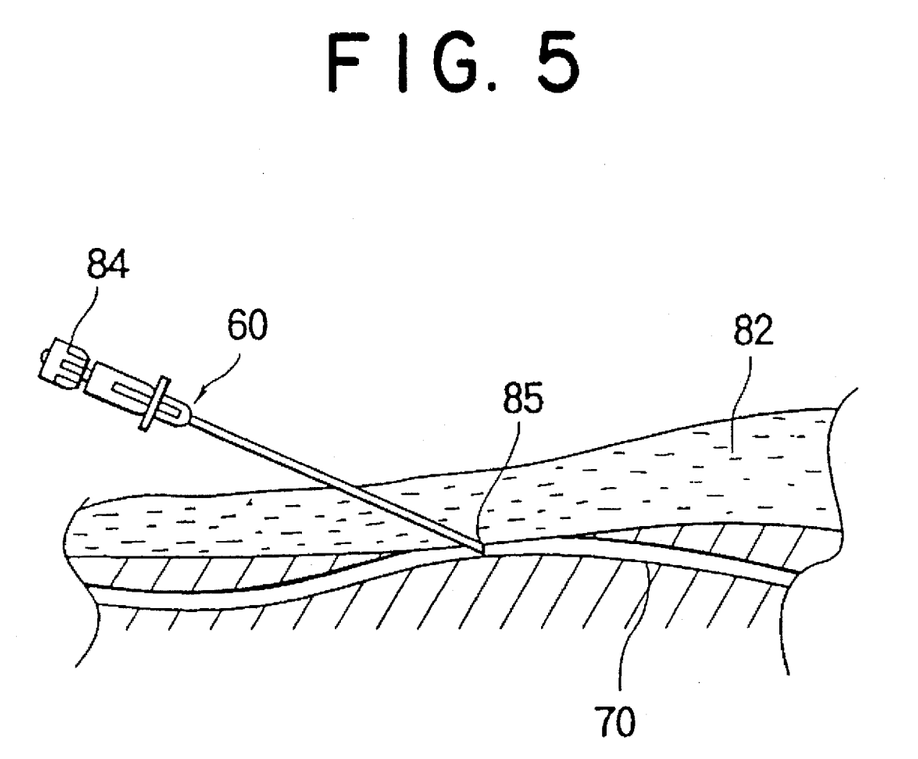
FIG. 5 is a schematic view showing the method of use of the balloon catheter set.

The catheter set of the embodiment includes, in addition to the afore-mentioned balloon catheter 20, the retaining sheath 50 shown in FIG. 3, the needle 60 shown in FIG. 5, the guide wire 62 shown in FIG. 3, a not shown dilator, etc.

The retaining sheath 50 shown in FIG. 3 has a sheath body 53 with a distal end 53a inserted into the blood vessel 70 of a patient. The proximal end 53b of the sheath body 53 has a flange portion formed at it, where the flange portion is interposed together with the hemostatic valve 54 between the sheath base portion 52 and cap portion 55. The sheath base portion 52 and cap portion 55 are connected by screwing. At the outer circumference of the cap portion 55 is formed a handle 56 for affixing to the surface of the body of the patient by surgical thread etc.

The length of the sheath body 53 of the retaining sheath 50 is for example 50 to 200 mm, preferably near 100 mm. The inside diameter is preferably 0.8 to 3.0 mm or so in view of the need to pass the catheter tube 24 shown in FIG. 1. Further, the thickness of the sheath body 53 is preferably as thin as possible from the viewpoint of lightening the discomfort on the patient, but a predetermined rigidity is required also, so 0.05 to 0.4 mm is preferable. The sheath body 53 is for example comprised of polyfluoroethylene, polyurethane, polyethylene, etc.

Figure 4A:
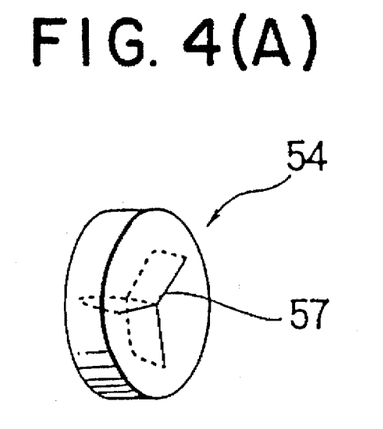
FIG. 4a–d is a perspective view showing the forms of the hemostatic valve used in the retaining sheath.

The hemostatic valve 54, for example, as shown in FIG. 4A, is comprised of a disk shaped piece of rubber, at the center of which is formed slits 57. The balloon portion 22 and catheter tube 24 shown in FIG. 1 are inserted through the slits 57 into the sheath body 53 and guided to the blood vessel 70. The blood in the blood vessel is sealed by the hemostatic valve 54 and will not flow outside. The thickness of the hemostatic valve 54 is for example about 0.05 to 2 mm.

Figure 4B:
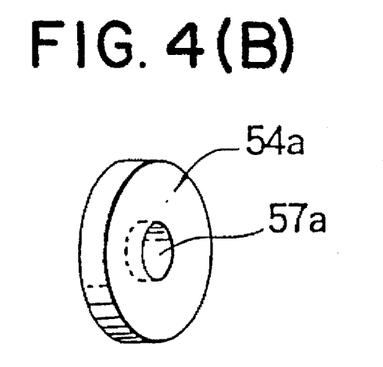
Figure 4C:
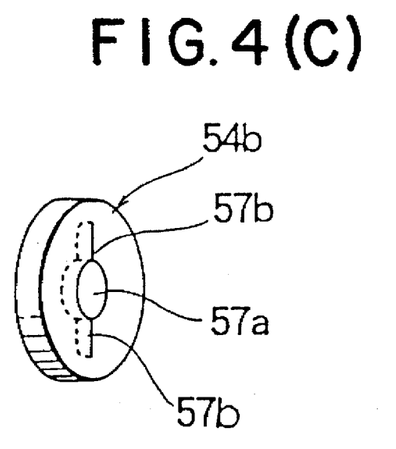
Figure 4D:
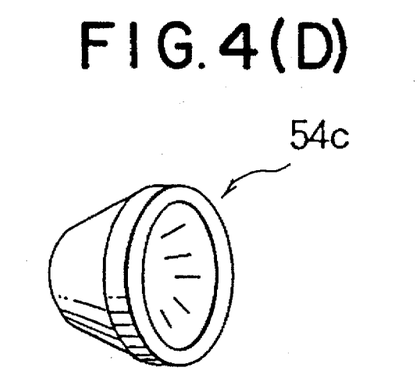

Note that the hemostatic valve is not limited to a piece of rubber of the shape shown in FIG. 4A. It may be comprised by the disk shaped rubber piece 54a having a through hole 57a in the center as shown in FIG. 4B, it may be a disk shaped rubber piece 54b formed with slits 57b at the two sides of the through hole 57a as shown in FIG. 4C, and it may be a conical cylindrical rubber piece 54c as shown in FIG. 4D.

Next, an explanation will be made of the method of insertion of the balloon catheter 20 using the catheter set of this embodiment.

First, as shown in FIG. 5, a needle 60 is inserted from the surface of the skin 82 of the patient to position its distal end in the blood vessel 70 to make an incision 85. Next, a styler 84 inserted through the inside of the needle is pulled out. A guide wire 62 (see FIG. 3) is inserted into the blood vessel 70 from the hole from which the styler 84 was pulled out.

Next, the needle 60 is pulled out along the inserted guide wire 62, then a small diameter dilator (not shown) with a front taper is inserted into the incision 85 of the blood vessel along the guide wire 62 to push wider the incision 85. Next, the small diameter dilator is pulled out along the guide wire, then a relatively large diameter tapered retaining sheath dilator (not shown) is inserted along the guide wire 62 into the blood vessel 70 in the state inserted in the retaining sheath 50.

Next, as shown in FIG. 3, the retaining sheath dilator is pulled out in the state with the distal end 53a of the retaining sheath 50 inserted in the blood vessel 70. Then, the balloon portion 22 and catheter tube 24 of the balloon catheter 20 shown in FIG. 1 are inserted into the blood vessel 70 through the retaining sheath 50 shown in FIG. 3. At the time of insertion, the balloon portion 22 is superposed over an outer diameter less than the inner diameter of the retaining sheath 50. Further, at the time of insertion, the guide wire 62 is passed into the inner tube 30 of the balloon catheter 20. When the balloon catheter 20 is inserted, bleeding from the blood vessel 70 is prevented by the action of the hemostatic valve 54 of the retaining sheath 50.

Figure 6:
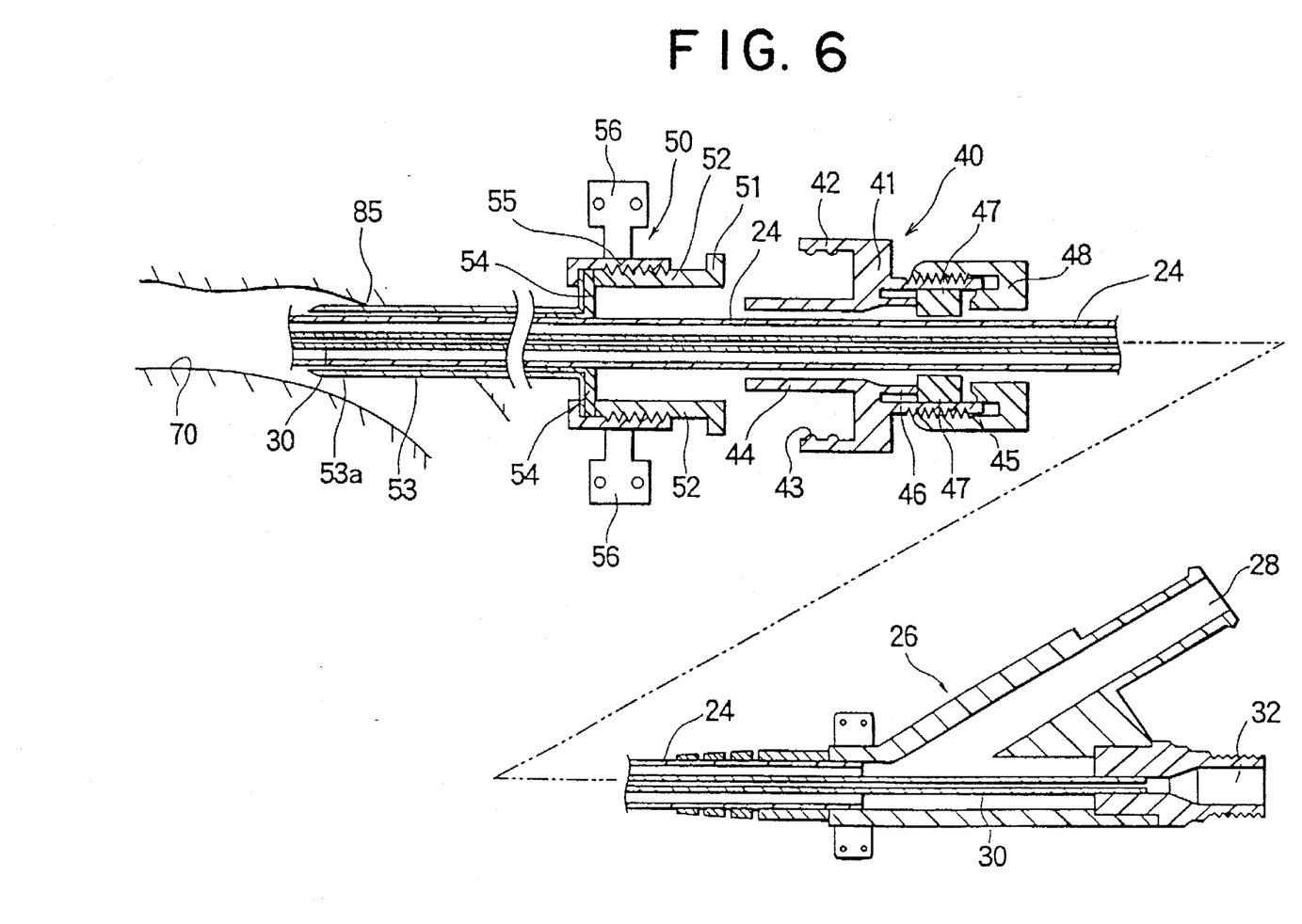
FIG. 6 is a cross-sectional view showing the method of use of the balloon catheter set.

When the balloon portion 22 and catheter tube 24 of the balloon catheter 20 are inserted at the prescribed positions in the blood vessel 70 through the retaining sheath 50, next, in the present embodiment, as shown in FIG. 6, a positioning plug 40 attached to the outer circumference of the catheter tube 24 outside the body so as to be movable in the axial direction is inserted along the axial direction of the catheter tube 24 in the direction of the incision 85 of the blood vessel 70, that is, in the direction of the retaining sheath 50.

After this, as shown in FIG. 7, the threaded projection 43 of the first outer tube 42 of the positioning plug 40 is engaged with the flange portion 51 of the sheath base 52 to connect the positioning plug 40 and the retaining sheath 50. Note that the means of connection of the positioning plug 40 and the retaining sheath 50 is not limited to the threaded projection 43 and the flange portion 51 and that use may be made of a screw engagement means or other means as well.

Figure 8:
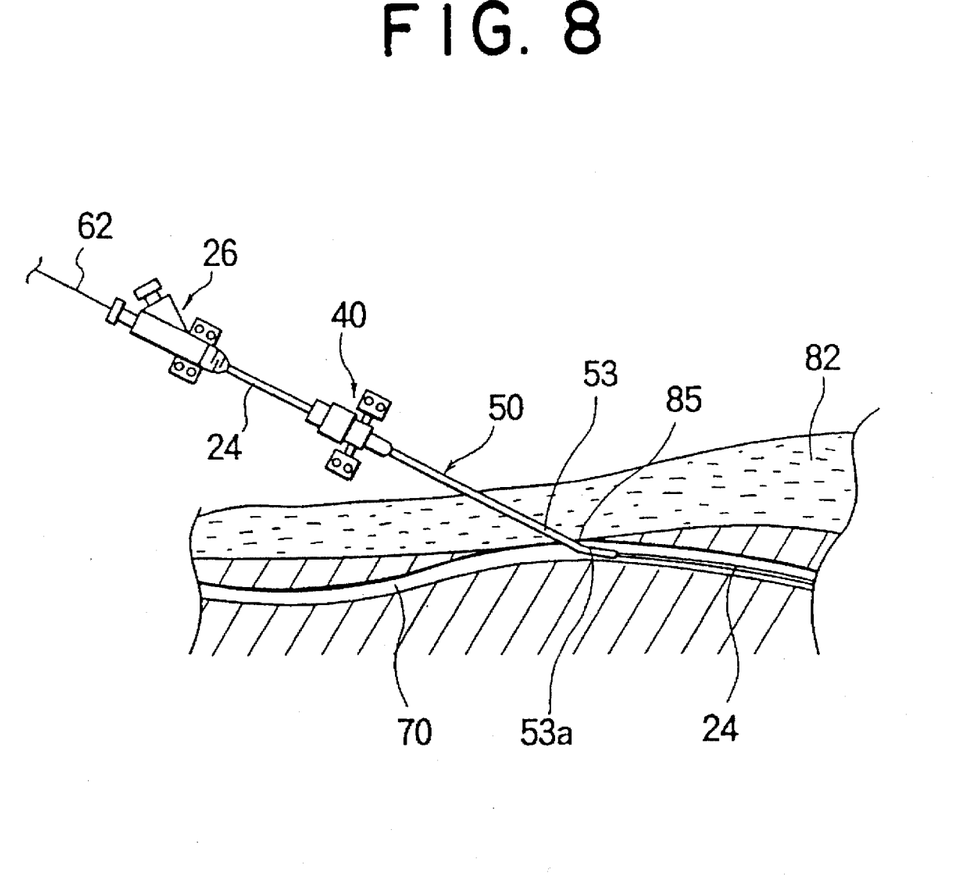
FIG. 8 is a cross-sectional view showing the state of use of the balloon catheter set.

Next, the cap 48 of the positioning plug 40 is screwed on to the plug body 41, whereupon the holding ring 47 is compressed in the axial direction and presses against the outer circumference of the catheter tube 24. As a result, the positioning plug 40 is affixed to the outer circumference of the catheter tube 24 and the positioning plug 40 is affixed to the retaining sheath 50. This state is shown in FIG. 8. Note that the holding ring 47 also has the function of a homostatic valve.

Next, the handle 56 of the retaining sheath 50 is affixed to the surface of the body of the patient using surgical thread etc., thereby affixing the retaining sheath 50 to the patient and positioning the catheter tube 24 simultaneously. Accordingly, in the embodiment, the portion to be affixed to the skin of the patient becomes smaller, the discomfort on the patient can be lightened, and further the portion to be disinfected becomes smaller and the work efficiency is improved.

Note that the reason why it is important to position the catheter tube 24 with respect to the skin of the patient is to keep the position of insertion of the catheter tube 24 and the balloon portion 22 from shifting in the longitudinal direction of the blood vessel 70. As shown in FIG. 2, the balloon portion 22 is positioned at a predetermined position in the arterial blood vessel near to the heart i and is made to expand and contract there so as to assist the heart function, so it is important that the catheter tube 24 does not shift in position in the blood vessel 70. Further, the length of the blood vessel differs depending on the person, so the positioning plug 40 must be attached to the outer circumference of the catheter tube 24 so as to be movable in the axial direction. In general, almost all catheter tubes, not only catheter tubes for the IABP method, have positions optimal for retention which have been determined anatomically, but the absolute values can not be determined due to individual differences.

After this, the wire 62 is removed from the blood vessel 70, the driving console 10 shown in FIG. 2 is connected to the bifurcation 26 of the balloon catheter 20, and the IABP treatment is performed by the balloon catheter 20.

Figure 9:
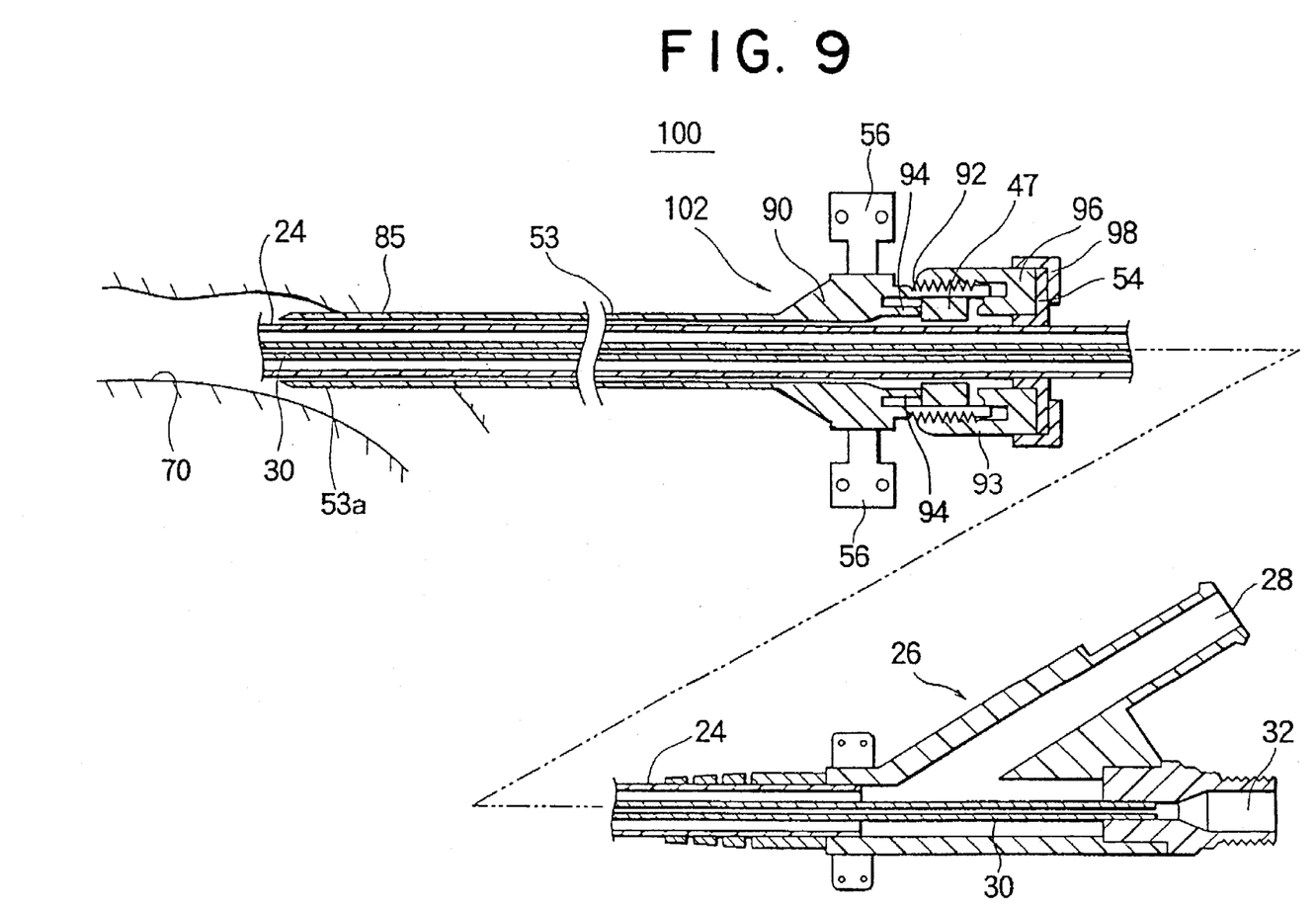
FIG. 9 is a cross-sectional view showing an example of use of a balloon catheter set according to a second embodiment of the present invention.

Next, an explanation will be made of a second embodiment of the present invention based on FIG. 9. In the another set of the balloon catheter 100 according to the embodiment shown in FIG. 9, the holding ring 47 is attached together with the hemostatic valve 54 to the proximal end of a retaining sheath 102 without attaching the positioning plug 40 having the holding ring 47 shown in FIG. 1 to the outer circumference of the catheter tube 24 in the balloon catheter.

That is, in the retaining sheath 102 of this embodiment, the sheath body 53 is connected to the sheath base 90 by adhesion, heat bonding, integral molding, or other means. A handle 56 is formed at the outer circumference of the sheath base 90. At the proximal end of the sheath base 90 are formed substantially concentrically an outer tube 92 and an inner tube 94, a body 93 of a cap 96 being screwed on the outer circumference of the outer tube 92. At the inner circumference side of the outer tube 92 is disposed a holding ring 47. By screwing the body 93 of the cap 96 on the outer tube 92, the holding ring 47 is compressed in the axial direction and presses against the outer 26 circumference of the catheter tube 24 to affix the same. At the proximal end of the cap 96 is attached the hemostatic valve 54 with an adapter 98. The adapter 98 is connected to the cap 96 by adhesion, heat bonding, screwing, or other means.

The rest of the construction of the balloon catheter set according to this embodiment is similar to that of the embodiment shown in FIGS. 1 to 8.

In this embodiment, like in the first embodiment, the distal end 53a of the sheath body 53 of the retaining sheath 102 is inserted into the blood vessel 70. After this, the balloon portion and the catheter tube 24 are inserted through the retaining sheath 102 to the prescribed position in the blood vessel. At this time, since the hemostatic valve 54 is attached to the proximal end of the retaining sheath 102, it is possible to prevent to a great extent bleeding of the patient. After this, the cap 96 attached to the proximal end of the retaining sheath 102 is operated to compress the holding ring 47 in the axial direction and press it to the outer circumference of the catheter tube 24. As a result, the outer circumference of the catheter tube 24 is affixed to the retaining sheath 102 and the catheter tube 24 is positioned with respect to the retaining sheath 102. Next, by affixing the retaining sheath 102 to the skin of the patient, the retaining sheath 102 can be affixed to the patient and the catheter tube 24 can be positioned simultaneously.

Therefore, in the present embodiment, the portion affixed to the skin of the patient becomes smaller, the discomfort on the patient is lightened, the portion for disinfection becomes smaller, and the work efficiency is improved. In particular, in this embodiment, compared with the first embodiment, it is possible to position the catheter tube 24 with respect to the retaining sheath 102 without the use of the positioning plug 40, the operability is further improved, and a contribution is made to the reduction of the number of parts.

Note that the present invention is not limited to the above embodiments and that various modifications can be made within the scope of the invention.

For example, in the above embodiments, provision was made of the handle 56 at the retaining sheath 50 side, but it is also possible to provide it at the positioning plug 40 side. This is because, in the present invention, it is sufficient to affix just one of the retaining sheath 50 and positioning plug 40 to the patient's skin.

Third Embodiment

Figure 10:
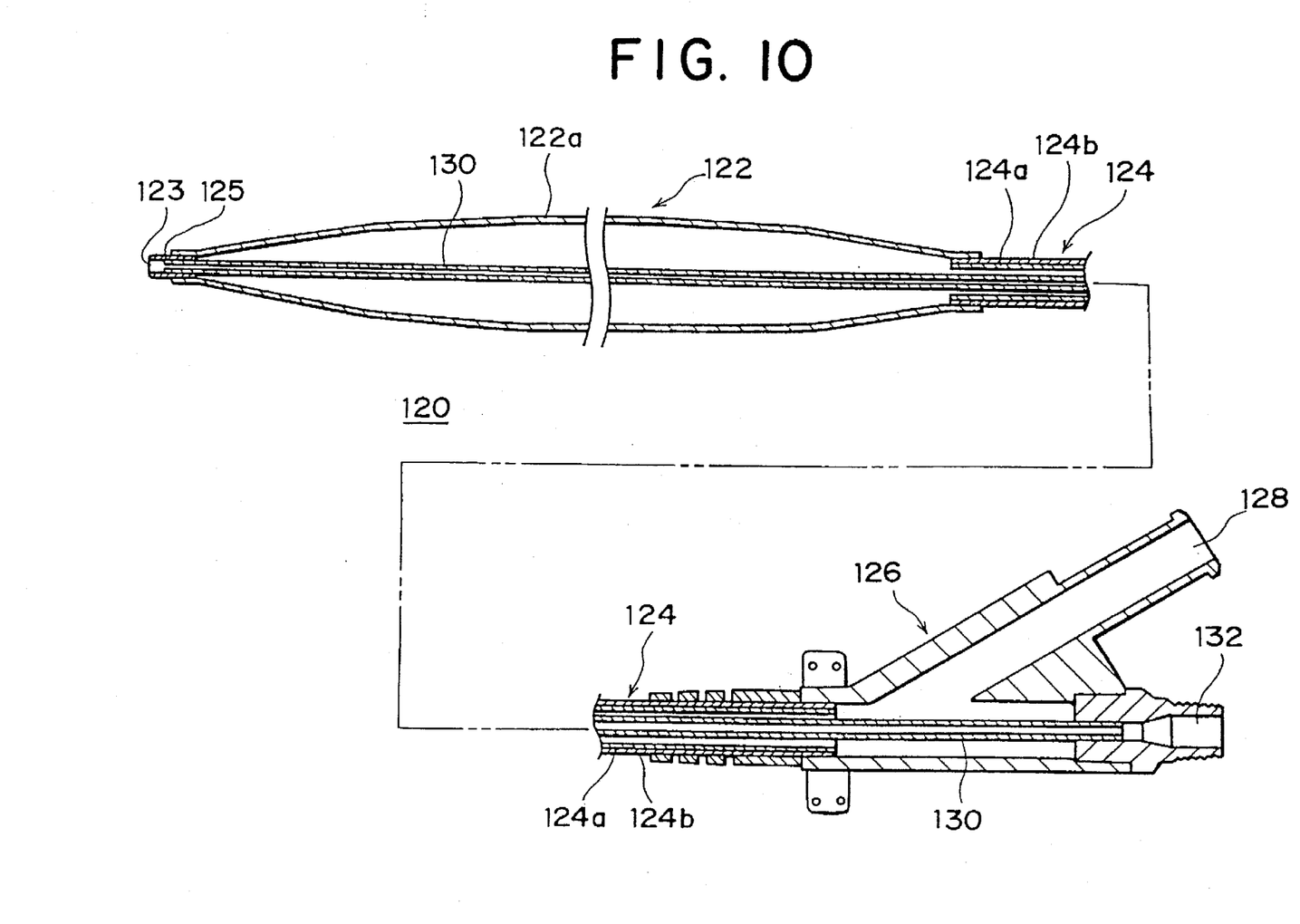
FIG. 10 is a schematic cross-sectional view of a balloon catheter according to a third embodiment of the present invention.

As shown in FIG. 10, a balloon catheter 120 according to a third embodiment of the present invention has a balloon portion 122 which expands and contracts in timing with the beat of the heart. The balloon portion 122 has substantially the same construction as the balloon portion 22 as showing FIG. 1.

At the distal end of the balloon portion 122 there is attached by a means such as heat bonding or adhesion a front tip portion 125 with a blood port 123 formed in it.

At the inner circumference of the front tip portion 125 is attached the distal end of the inner tube 130 by heat bonding or adhesion.

At the proximal end of the balloon portion 122 is connected the distal end of the catheter tube 124. The shuttle gas is introduced to or released from the inside of the balloon portion 122 through the catheter tube so as to make the balloon film 122a of the balloon portion 22 expand or contract. The balloon portion 122 and the catheter tube 124 are connected by heat bonding or adhesion by an adhesive such as an ultraviolet ray curable resin.

The inner tube 130 extends in the axial direction inside the balloon portion 122 and the catheter tube 124 and is communicated with the later mentioned blood pressure measurement port 132 of the bifurcation 126. The inside is not communicated with the inside of the balloon portion 122. The inner tube 130 has substantially the same construction as the inner tube 30 of the first embodiment shown in FIG. 1.

At the proximal end of the catheter tube 124 is connected the bifurcation 126 positioned outside the patient's body. The bifurcation 126 is affixed to the proximal end of the catheter tube 124 by a means such as heat bonding or adhesion. At the bifurcation 126 are formed a shuttle gas port 128 for introducing or releasing shuttle gas into or from the inside of the catheter tube 124 and the balloon portion 122 and a blood pressure measurement port 132 communicated with the inside of the inner tube 130.

The shuttle gas port 128 is connected to a driving console 10, for example, as shown in FIG. 2. The relationship between the driving console 10 and the bifurcation 126 is substantially the same as that between the driving console 10 and the bifurcation 26 of the first embodiment.

Figure 11:
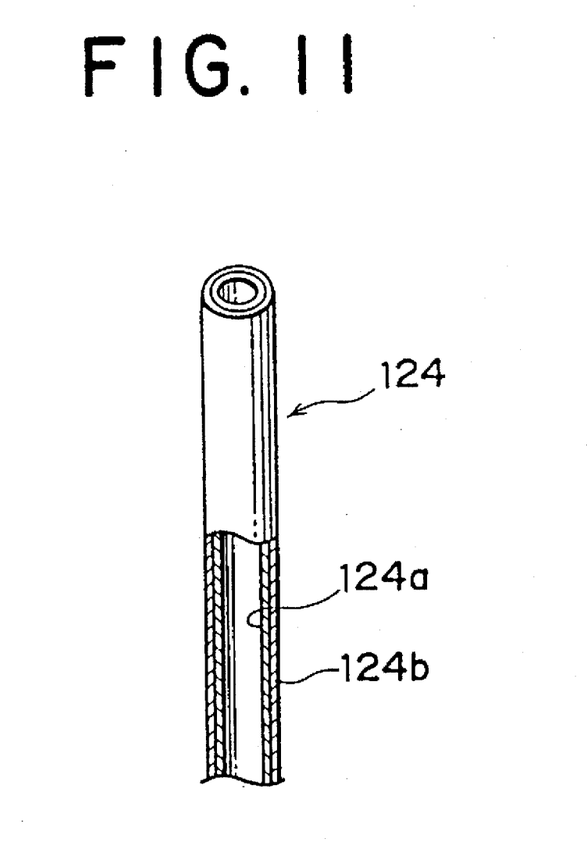
FIG. 11 is a cutaway perspective view of a catheter tube shown in FIG. 10.

In this embodiment, as shown in FIGS. 10 and 11, the catheter tube 124 is comprised of a double-tube construction of a base tube 124a and a surface tube 124b. The base tube 124a is comprised of a hard plastic with a linear elastic modulus of at least 100 kg/mm$^2$, more specifically, is comprised of a polyamide resin, a polyimide resin, a fluorocarbon resin (PFA, PTFE, ETFE, etc.), a polyvinyl difluoride resin (PVDF), etc. Further, the surface tube 124b is comprised of an anti-thrombogenic material, more specifically, is comprised of a polyurethane.

The upper limit of the linear elastic modulus of the base tube 124a is preferably 10,000 kg/mm$^2$. If the linear elastic modulus of the base tube 124a is more than 10,000 kg/mm$^2$, the catheter tube 124 tends to be too stiff, it is not easy to handle the balloon catheter 120 when insertion and there is a danger of damaging the blood vessel etc.

The inside diameter and thickness of the catheter tube 124 comprised of the base tube 124a and the surface tube 124b are not particularly limited, but the inside diameter is preferably 1.5 to 4.0 mm and the thickness is preferably 0.05 to 0.4 mm. Further, the thickness of the base tube 124a is 0.03 to 0.35 mm.

The catheter tube 124 comprised of the base tube 124a and the surface tube 124b may for example be formed by a double-tube extrusion molding method. Further, the base tube 124a and the surface tube 124b may be separately formed and then adhered or heat bonded at a later step. In addition, the surface tube 124b formed on the outer circumference of the base tube 124a may be formed by a solution dipping method, spray method, etc. As an adhesives between the base tube 124a and the surface tube 124b, a polyisocyanate type adhesives is preferably used. The reason why use is made of the polyisocyanate type adhesives is that the polyisocyanate reacts with polyurethane with heating and strongly adheres to the same.

Next, an explanation will be made of a method for production of a balloon catheter according to another embodiment of the present invention.

Figures 12A, 12B, 12C:
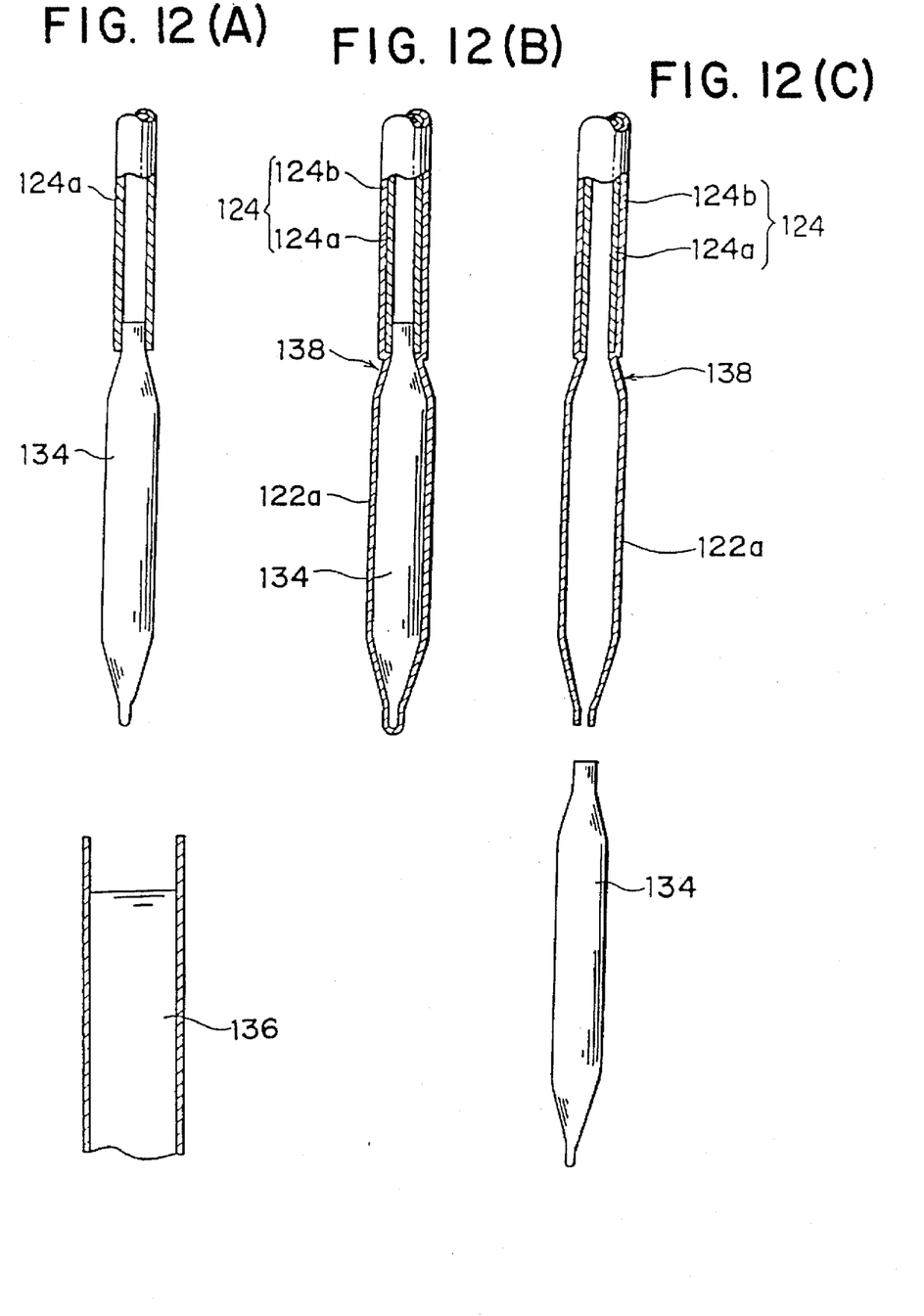
FIGS. 12A, 12B, and 12C are schematic views showing the method for production of a balloon catheter according to another embodiment of the present invention.

In this embodiment, as shown in FIG. 12A, first, a base tube 124a comprised of a hard plastic with a linear elastic modulus of at least 100 kg/mm$^2$ is prepared.

Next, a male mold 134 for forming the balloon portion is attached to the distal end of the base tube 124a. The male mold 134 is comprised for example of a stainless steel rod member and has an outer circumferential shape matching the inner circumferential shape of the balloon film desired to be obtained. Next, a layer of a solution of the anti-thrombogenic material is formed using the dipping method etc. on the outer circumference of the male mold 34 and base tube 124a. That is, the base tube 124a with the male mold 134 mounted at its distal end is immersed in a solution 136 of the anti-thrombogenic material.

As the solution 136 of the anti-thrombogenic material, use is preferably made of a polyurethane solution incorporating a solvent of tetrahydrofuran (THF) etc. The viscosity of the solution 136 is adjusted in advance to 100 to 1000 cp, preferably 1000 to 5000 cp.

The number of times and the frequency of dipping of the base tube 124a with the male mold 34 attached to it in the resin solution 136 are not particularly limited and are performed until a thin film of the solution of a desired thickness is formed on the outer circumference of the male mold 134 and the base tube 124a. Note that in the present invention, the means for forming the thin film layer of the solution on the outer circumference of the male mold 134 and the base tube 124a is not particularly limited to the dipping method. Use may be made of the spray method etc.

Next, as shown in FIG. 12B, the male mold 134 on whose outer circumference is formed a thin film layer 138 of the solution is taken out from the solution 136. The thin film layer 138 is dried to evaporate the solvent contained in the thin film and integrally form the surface tube 124b and the balloon film 122a on the outer circumference of the base tube 124a and the outer circumference of the male mold 134. In the drying step of the thin film layer 138, for example, air drying is performed at ordinary temperature in the air for several minutes to several hours, preferably for one hour or so, then drying is performed at an atmospheric temperature of 80° to 90° C. for 3 hours to 24 hours, preferably for 10 to 14 hours.

After this, as shown in FIG. 12C, the distal end of the balloon film 122a is partially cut off and the male mold 134 is withdrawn from there, thereby obtaining a balloon catheter comprised of a balloon film 122a and the surface tube 124b of the catheter tube 124 formed integrally together. In actuality, the front tip portion 125 shown in FIG. 10 may be attached to the distal end of the balloon film 122a and, when necessary, the inner tube 130 may be attached. Note that in the present invention, it is not absolutely necessary to attach the hollow inner tube 130 shown in FIG. 10. It is also possible to construct a balloon catheter without a hollow inner tube 130. In this case, no blood port 123 is formed at the distal end of the front tip portion 125.

Next, the present invention will be explained with reference to specific examples. The present invention, however, is not limited to the following examples.

EXAMPLE 1

As the inner tube 130 shown in FIG. 10, use was made of a fine polyamide tube of an outer diameter of 1.4 mm and a thickness of 200 µm. As the balloon film 122a, use was made of a polyurethane film of a thickness of 0.1 mm. The outer diameter of the balloon portion 122 when expanded was 15 mm, the inner volume of the balloon portion was 30 cc, and the length in the axial direction was 230 mm. As the catheter tube 124, use was made of a two-layer extruded tube comprised of a base tube 124a and a surface tube 124b. The base tube 124a was comprised of a polyamide and had an outer diameter of 3.0 mm, a thickness of 180 µm, and a linear elastic modulus at 37° C. of 440 kg/mm$^2$. Further, the surface tube 124b was comprised of a polyurethane and had an outer diameter of 3.10 mm and a thickness of 50 μm. For the adhesion of the distal end of the catheter tube 124 and the end of the balloon film 122a, use was made of heat bonding.

This balloon catheter was passed through an acrylic simulated blood vessel of an inside diameter of 35 mm and a length of 350 mm. Physiological saline solution adjusted in temperature to 37° C. was passed through this simulated blood vessel at a flow rate of 10 cm/sec. After 24 hours, the state of movement of the balloon portion 22 was investigated. The results are shown in Table 1.

TABLE 1

|  | Distance of movement |
| --- | --- |
| Ex. 1 | 0.2 cm |
| Ex. 2 | 0.0 cm |
| Ex. 3 | 0.0 cm |
| Comp. Ex. 1 | 5.0 cm |

EXAMPLE 2

A balloon catheter was prepared similar to that of Example 1 except that the base tube was comprised of a polyamide (linear elastic modulus of 1900 kg/mm$^2$). The distance of movement was investigated for this balloon catheter in the same way as with Example 1. The results are shown in Table 1.

EXAMPLE 3

A balloon catheter was prepared similar to that of Example 1 except for the following method. The base tube was comprised of a polyamide (linear elastic modulus of 1900 kg/mm$^2$). The outside peripheral surface of the base tube was coated with polyisocyanate, then the base tube was air dried and then dried at 120° C. for one hour. After that, on the outside peripheral surface of the base tube was coated a polyurethane layer by dipping in a solution where polyurethane was dissolved in a solution of tetrahydrofuran. This was again air dried, and then dried at 120° C. for 5 hours to obtain the surface tube on the outside peripheral surface of the base tube. It was observed that the surface tube was strongly adheres to the base tube, because the polyisocyanate on the base tube reacted with polyurethane with heating.

The distance of movement was investigated for this balloon catheter in the same way as with Example 1. The results are shown in Table 1.

COMPARATIVE EXAMPLE 1

A balloon catheter was prepared similar to that of Example 1 except that the catheter tube was comprised of a single layer polyurethane tube (linear elastic modulus of 210 kg/mm$^2$) with an outer diameter of 3.10 mm and a thickness of 230 μm. The distance of movement was investigated for this balloon catheter in the same way as with Example 1. The results are shown in Table 1.

Evaluation

As shown in Table 1, it was confirmed that there was less pushing back by the simulated flow of blood with the balloon catheters of Examples 1, 2 and 3 than with the balloon catheter of Comparative Example 1.

What is claimed is:

1. A balloon catheter for intra-aortic balloon pumping comprising:

a catheter tube defining a first lumen and having a proximal end and a distal end, each end defining an opening, said catheter tube being comprised of a base tube made of a hard plastic with a linear elastic modulus of at least 100 kg/mm$^2$ selected from the group consisting a polyamide resin, a polyimide resin, a fluorocarbon resin and a polyvinyl difluoride resin, and a surface tube made of an anti-thrombotic polyurethane resin bonded to the outer circumference of said base tube with an adhesive;

an inner tube defining a second lumen and having a proximal end and a distal end, each end defining an opening, said inner tube being inserted into the first lumen of the catheter tube so that the distal end of the inner tube extends beyond the distal end of the catheter tube; and a balloon portion having a proximal end and a distal end and defining an inner space, said balloon portion comprised of a cylindrical thin film, the proximal end of the balloon portion being connected to the distal end of said surface tube and the distal end of the balloon portion being connected to the distal end of the inner tube so that the inner space of the balloon portion communicates with the first lumen so that shuttle gas which is introduced and released into and from the inner space of the balloon portion through the first lumen expands and contracts the balloon portion in timing with a beating heart.

2. The balloon catheter as set forth in claim 1, wherein a polyisocyanate adhesive is provided between said base tube and surface tube to bond said surface tube to the circumference of said base tube.

3. A balloon catheter for intra-aortic balloon pumping comprising:

a catheter tube defining a first lumen and having a proximal end and a distal end, each end defining an opening, said catheter tube being comprised of a base tube made of a hard plastic with a linear elastic modulus of at least 100 kg/mm$^2$ selected from the group consisting a polyamide resin, a polyimide resin, a fluorocarbon resin and a polyvinyl difluoride resin, and a surface tube made of an anti-thrombotic polyurethane resin bonded to the outer circumference of said base tube;

an inner tube defining a second lumen and having a proximal end and a distal end, each end defining an opening, said inner tube being inserted into the first lumen of the catheter tube so that the distal end of the inner tube extends beyond the distal end of the catheter tube; and a balloon portion having a proximal end and a distal end and defining an inner space, said balloon portion comprised of a cylindrical thin film and being formed integrally with said surface tube so that the proximal end of the balloon portion is bonded to the distal end of said base tube and the distal end of the balloon portion being connected to the distal end of the inner tube so that the inner space of the balloon portion communicates with the first lumen so that shuttle gas which is introduced and released into and from the inner space of the balloon portion through the first lumen expands and contracts the balloon portion in timing with a beating heart.

4. The balloon catheter as set forth in claim 3, wherein a polyisocyanate adhesive is provided between said base tube and surface tube to bond said surface tube to the circumference of said base tube.

* * * * *